(12) United States Patent
Webster et al.

(10) Patent No.: US 7,833,283 B2
(45) Date of Patent: *Nov. 16, 2010

(54) MATERIAL AND METHOD FOR PROMOTING TISSUE GROWTH

(75) Inventors: Thomas Jay Webster, Lafayette, IN (US); Karen Marie Haberstroh, Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 35 days.

This patent is subject to a terminal disclaimer.

(21) Appl. No.: 10/362,148

(22) PCT Filed: Aug. 15, 2002

(86) PCT No.: PCT/US02/25812

§ 371 (c)(1),
(2), (4) Date: Feb. 19, 2003

(87) PCT Pub. No.: WO03/015836

PCT Pub. Date: Feb. 27, 2003

(65) Prior Publication Data

US 2004/0038063 A1 Feb. 26, 2004

Related U.S. Application Data

(60) Provisional application No. 60/312,800, filed on Aug. 16, 2001.

(51) Int. Cl.
*A61F 2/02* (2006.01)
*A61K 9/00* (2006.01)

(52) U.S. Cl. .................................................. 623/23.72

(58) Field of Classification Search ... 623/23.72–23.76, 623/23.58, 23.59, 1.39, 1.4–1.49, 1.5–1.54; 428/532, 480, 422.8; 424/400, 93.1
See application file for complete search history.

(56) References Cited

U.S. PATENT DOCUMENTS

| | | | |
|---|---|---|---|
| 4,776,853 A | 10/1988 | Klement et al. | |
| 4,795,436 A * | 1/1989 | Robinson | 424/422 |
| 4,902,508 A | 2/1990 | Badylak et al. | |
| 4,998,239 A * | 3/1991 | Strandjord et al. | 369/275.1 |
| 5,281,422 A | 1/1994 | Badylak et al. | |
| 5,292,328 A | 3/1994 | Hain et al. | |
| 5,306,311 A | 4/1994 | Stone et al. | |
| 5,372,821 A | 12/1994 | Badylak et al. | |
| 5,415,704 A | 5/1995 | Davidson | |
| 5,573,784 A | 11/1996 | Badylak et al. | |
| 5,733,337 A | 3/1998 | Carr, Jr. et al. | |
| 5,744,515 A | 4/1998 | Clapper | |
| 6,106,913 A | 8/2000 | Scardino et al. | |
| 6,183,255 B1 | 2/2001 | Oshida | |
| 6,262,017 B1 | 7/2001 | Dee et al. | |
| 6,270,347 B1 | 8/2001 | Webster et al. | |
| 6,291,070 B1 | 9/2001 | Arpac et al. | |
| 6,319,264 B1 | 11/2001 | Tormala et al. | |
| 6,344,367 B1 * | 2/2002 | Naya et al. | 438/32 |
| 6,355,198 B1 * | 3/2002 | Kim et al. | 264/259 |
| 6,368,859 B1 | 4/2002 | Atala | |
| 6,396,208 B1 * | 5/2002 | Oda et al. | 313/504 |
| 6,572,672 B2 | 6/2003 | Yadav et al. | |
| 6,669,706 B2 | 12/2003 | Schmitt et al. | |
| 6,689,374 B2 * | 2/2004 | Chu et al. | 424/423 |
| 6,756,286 B1 * | 6/2004 | Moriceau et al. | 438/459 |
| 6,790,455 B2 * | 9/2004 | Chu et al. | 424/423 |
| 6,797,514 B2 * | 9/2004 | Berenson et al. | 435/325 |
| 6,805,898 B1 * | 10/2004 | Wu et al. | 427/2.25 |
| 6,881,249 B2 * | 4/2005 | Anderson et al. | 106/31.03 |
| 6,929,539 B2 * | 8/2005 | Schutz et al. | 451/534 |
| 2002/0167118 A1 | 11/2002 | Billiet et al. | |
| 2002/0173033 A1 | 11/2002 | Hammerick et al. | |
| 2002/0173213 A1 | 11/2002 | Chu et al. | |
| 2003/0040809 A1 | 2/2003 | Goldmann et al. | |
| 2003/0050711 A1 | 3/2003 | Laurencin et al. | |
| 2004/0028875 A1 | 2/2004 | Van Rijn et al. | |
| 2004/0104672 A1 * | 6/2004 | Shiang et al. | 313/506 |
| 2004/0131753 A1 | 7/2004 | Smith et al. | |
| 2004/0171323 A1 | 9/2004 | Shalaby | |
| 2004/0241211 A9 | 12/2004 | Fischell et al. | |
| 2006/0173471 A1 | 8/2006 | Carr, Jr. et al. | |

FOREIGN PATENT DOCUMENTS

| | | |
|---|---|---|
| WO | WO 97/25999 | 7/1997 |
| WO | WO 01/55473 | 8/2001 |
| WO | WO 03/015836 | 2/2003 |

OTHER PUBLICATIONS

Jean-Louis Pariente et al., "In vitro biocompatibility assessment of naturally derive and synthetic biomaterials using normal human urothelial cells," *J. Biomed. Mater. Res.*, 55(1), (2001), pp. 33-39.

Malachy J. Gleeson et al., "The use of alloplastic biomaterials in bladder substitution," *J. Urol.*, 148, (1992), pp. 1377-1382.

Janeta Nikolovski et al., Smooth muscle cell adhesion to tissue engineering scaffolds, *Biomat.*, 21, (2000), pp. 2025-2032.

Anthony Atala et al., "Implantation in vivo and retrieval of artificial structures consisting of rabbit and human urothelium and human bladder muscle," *J. Urol.*, 150, (1993), pp. 608-612.

M. J. Lydon et al., "Cellular interactions with synthetic polymer surfaces in culture," *Biomat.* 6 (1985), pp. 396-402.

A. S. G. Curtis et al., "Adhesion of cells to polystyrene surfaces," *J. Cell Biol.*, 97, (1983), pp. 1500-1506.

Joseph A. Chinn et al., "Enhancement of serum fibronectin adsorption and the clonal plating efficiencies of Swiss mouse 3T3 fibroblast and MM14 mouse myoblast cells on polymer substrates modified by radiofrequency plasma deposition," *J. Colloid Interface Sci.*, 127, (1989), pp. 67-87.

(Continued)

*Primary Examiner*—Alvin J. Stewart
(74) *Attorney, Agent, or Firm*—Barnes & Thornburg LLP (57) ABSTRACT

A composition for promoting tissue growth which includes a material for placing in contact with animal tissue.

15 Claims, 10 Drawing Sheets

OTHER PUBLICATIONS

Paul Goldhaber, "The influence of pore size on carcinogenicity of subcutaneously implanted Millipore filters," *Proc. Am. Assoc. Cancer Res.*, 3 (1961), p. 28.

J. Brauker et al., "Neovascularization of immunoisolation membranes: the effect of membrane architecture and encapsulated tissue," *Transplant Proc.*, 24, (1992); p. 2924.

Paul Weiss, "In vitro experiments on the factors determining the course of the outgoing nerve fiber," *J. Exp. Zool.*, 68, (1945), pp. 393-448.

G. A. Dunn et al., "Alignment of fibroblasts on grooved surfaces described by a simple geometric transformation," *J. Cell Sci.*, 83, (1986), pp. 313-340.

J. Meyle et al., "Variation in contact guidance by human cells on a microstructured surface," *J. Biomed. Mater. Res.*, 29, (1995), pp. 81-88.

John A. Schmidt et al., "Macrophage response to microtextured silicone," *Biomat.*, 12, (1992), pp. 385-389.

Mark A. Schubert et al., "Role of oxygen in biodegradation of poly(etherurethane urea) elastomers," *J. Biomed. Mat. Res.*, 34, (1997), pp. 519-530.

M. Conley et al., "Effects of biodegradable polymer particles on rat marrow-derived stromal osteoblasts in vitro," *Biomaterials*, 19, (1998), pp. 1255-1268.

Susan L. Ishaug-Riley et al., "Three-dimensional culture of rat calvarial osteoblasts in porous biodegradable polymers," *Biomaterials* 19, (1998), pp. 1405-1412.

Susan L. Ishaug-Riley et al., "Human articular chondrocyte adhesion and proliferation on synthetic biodegradable polymer films," *Biomaterials*, 20, (1999), pp. 2245-2256.

Karen M. Haberstroh et al., "The Effects of Sustained Hydrostatic Pressure on Select Bladder Smooth Muscle Cell Functions," *The Journal of Urology*, vol. 162, (1999), pp. 2114-2118.

Paul Weiss, "Experiments on Cell and Axon Orientation in Vitro: The Role of Colloidal Exudates in Tissue Organization," Journal of Experimental Zoology, vol. 100(3), (1943), pp. 353-386.

J. Black and G. Hastings, "Handbook of Biomaterial Properties", *Chapman & Hall*, pp. 40-47 (1998).

Mankin et al., "Orthopaedic Basic Science—Chapter 1 Form and Function of Articular Cartilage", *American Academy of Orthopaedic Surgeons*, pp. 1-45, (1994).

Kay et al., "Nanostructured Polymer/Nanophase Ceramic Composites Enhance Osteoblast and Chondrocyte Adhesion", *Tissue Engineering*, vol. 8, No. 5, pp. 753-761, (2002).

Thapa et al., "An Investigation of Nano-stuctured Polymers for Use as Bladder Tissue Replacement Constructs", *Mat. Res. Soc. Symp. Proc.*, vol. 711, pp. 205-210, (2002).

Miller et al., An In Vitro Study of Nano-fiber Polymers for Guided Vascular Regeneration, *Mat. Res. Soc. Symp. Proc.*, vol. 711, pp. 201-204, (2002).

Jun et al., "An In Vitro Study of Chondrocyte Function on Nanostructured Polymer/Ceramic Formulations to Improve Cartilage Repair", *Nano 2002 Conference Abstract Book*, Orlando, FL, p. 269, (2002).

Tepper et al., "Nanosized alumina fibers," *American Ceramic Society Bulletin*, 80(6):57-60 (2001).

Webster et al., "An in vitro evaluation of nanophase alumina for orthopaedic/dental applications," *Bioceramics vol. 11 (Proceedings of the 11th International Symposium on Ceramics in Medicine)*, 273-76 (LeGeros & LeGeros eds., World Scientific Publishing Co, 1998).

Webster et al., "Hydroxylapatite with substituted magnesium, zinc, cadmium, and yttrium. II. Mechanisms of osteoblast adhesion," *J. Biomed. Mater. Res.*, 59:312-17 (2002).

Dee et al., "Design and function of novel osteoblast-adhesive peptides for chemical modification of biomaterials," *J. Biomed. Mater. Res.*, 40:371-77 (1998).

Webster et al., "Specific proteins mediate enhanced osteoblast adhesion on nanophase ceramics," *J. Biomed. Mater. Res.*, 51:475-83 (2000).

Webster et al., "Enhanced functions of osteoblasts on nanophase ceramics," *Biomaterials*, 21:1803-10 (2000).

Curtis & Wilkinson, "Review. Topographical control of cells," *Biomaterials*, 18(24):1573-83 (1997).

Puleo & Bizios, "RGDS tetrapeptide binds to osteoblasts and inhibits fibronectin-mediated adhesion," *Bone*, 12:271-76 (1991).

Siegel, "Creating nanophase materials," *Scientific American*, 275(6):74 (1996).

Webster et al., "Design and evaluation of nanophase alumina for orthopaedic/dental applications," *Nanostructured Materials*, 12:983-86 (1999).

Webster et al., "Enhanced surface and mechanical properties of nanophase ceramics to achieve orthopaedic/dental implant efficacy," *Key Engineering Materials*, vols. 192-195, pp. 321-24 (Proceedings of the 13th international symposium on ceramics in medicine, Bologna, Italy, 2000 (Trans Tech Publications, 2001).

Webster et al., "Mechanisms of enhanced osteoblast adhesion on nanophase alumina involve vitronectin," *Tissue Engineering*, 7(3):291-301 (2001).

Webster et al., "Nanoceramic surface roughness enhances osteoblast and osteoclast functions for improved orthopaedic/dental implant efficacy," *Scripta Mater.*, 44:1639-42 (2001).

Office Action for U.S. Appl. No. 10/634,292, US Patent & Trademark Office, Aug. 20, 2008.

Applicants response to U.S. Appl. No. 10/634,292 Office Action of Aug. 20, 2008, submitted Nov. 27, 2008.

Applicants supplemental response to U.S. Appl. No. 10/634,292 Office Action of Aug. 20, 2008, submitted Feb. 18, 2009.

Applicants supplemental IDS submitted in U.S. Appl. No. 10/634,292 on Feb. 18, 2009.

Office Action for U.S. Appl. No. 10/634,292, US Patent & Trademark Office, May 27, 2009.

Cellular Signaling in the Bladder, Laurence S. Baskin, Simon W. Hayward, Ronald A. Sutherland, Michael S. DiSandro, Axel A. Thomson and Gerald R. Cunha, Frontiers in Bioscience, 2, d592-595, Dec. 1, 1997.

The Effects of Sustained Hydrostatic Pressure on Select Bladder Smooth Muscle Cell Functions, Karen M. Haberstroh, Martin Kaefer, Alan B. Retik, Michael R. Freeman and Rena Bizios, The Journal of Urology, vol. 162, 2114-2118, Dec. 1999.

Preparation and characterization of poly(L-lactic acid) foams, Antonios G. Mikos, Amy J. Thorsen, Lisa A. Czerwonka, Yuan Bao, Robert Langer, Douglas N. Winslow, Joseph P. Vacanti, Polymer vol. 35 No. 5 1994.

Peroxisome Proliferator—Activated Receptor-y Agonists Increase Vascular Endothelial Growth Factor Expression in Human Vascular Smooth Muscle Cells, Kenjiro Yamakawa, Masayuki Hosoi, Hidenori Koyama, Shinji Tanaka, Shinya Fukumoto, Hirotoshi Morii, and Yoshiki Nishizawa, Biochemical and Biophysical Research Communications 271, 571-574 (2000).

Osteoblast adhesion on nanophase ceramics, Thomas J. Webster, Richard W. Siegel, Rena Bizios, Biomaterials 20 (1999) 1221-1227.

Fluorometric Assay of DNA in Cartilage Explants Using Hoechst 33258, Young-Jo Kim, Robert L. Y. Sah, Joe-Yuan H. Doong, and Alan J. Grodzinsky, Analytical Biochemistry 174, 168-176 (1988).

Modifications of a Specific Assay for Hydroxyproline in Urine, Kari I. Kivirikko, Ossi Laitinen and Darwin J. Prockop, Analytical Biochemistry 19, 249-255 (1967).

Extracellular matrix and integrin composition of the normal bladder wall, C.B. Wilson, J. Leopard, D.A. Cheresh, R.M. Nakamura, World J Urol (1996) 14:S30-S37.

\* cited by examiner

(a) Control (Untreated); d ≅ (10μm−15μm)

(b) 0.1N $HNO_3$ (10 min); d ≅ (100nm−1μm)

(c) 10N $HNO_3$ (30 min); d ≅ (50nm−100nm)

MATERIAL AND METHOD FOR PROMOTING TISSUE GROWTH

CROSS-REFERENCE TO RELATED APPLICATIONS

This application is a U.S. national counterpart application of international application serial no. PCT/US02/25812 filed Aug. 15, 2002, which claims priority to U.S. provisional application Ser. No. 60/312,800 filed Aug. 16, 2001.

TECHNICAL FIELD OF THE DISCLOSURE

The present invention generally relates to a material and associated method for promoting tissue growth. The present invention particularly relates to a nanostructured material for promoting tissue growth and an associated method which utilizes the nanostructured material for promoting tissue growth.

BACKGROUND OF THE DISCLOSURE

Tissue replacement materials (e.g., graft and implant materials) for tissues such as cardiovascular, tendon, muscle, bone, bladder, and heart, have attained considerable clinical and economic significance in modern medicine. For example, it is estimated that in 1986 $130 million was spent for vascular grafts alone, not including coronary artery bypass grafts.

Presently, there are two major approaches for the design and production of tissue replacement materials. One approach relies upon tissue replacement materials derived from natural sources. In particular, this approach utilizes various animal tissues as the tissue replacement material. However, a continuing problem with this approach is the inherent risk of transmitting an infectious disease associated with implanting an animal tissue in a human patient. Additional problems with the above described natural source approach include (i) not being able to acquire the appropriate animal tissue due to a limited supply and (ii) the possibility of ethical considerations associated with utilizing an animal tissue implant in a human being. In light of the above discussion it is apparent that utilizing an animal tissue as a tissue replacement material suffers from several drawbacks.

Another approach for the design and production of tissue replacement materials relies upon the use of synthetic substances, such as polytetrafluoroethylene and Dacron®. However, this approach also suffers from several drawbacks. For example, tissue replacement materials fabricated from synthetic substances do not sufficiently biomimic juxtaposed natural tissue and consequently, post-implantation, often fail to properly incorporate or integrate into the natural tissue. In addition, the mechanical characteristics (e.g., elasticity) of these tissue replacement materials are significantly different from the mechanical characteristics of the juxtaposed natural tissue. These differences can cause mechanical stresses between the tissue replacement material and the juxtaposed natural material, which in turn can lead to implant failure. As such, it is apparent that tissue replacement materials fabricated from synthetic substances also suffer from several drawbacks.

Therefore, in light of the above discussion, it is apparent that what is needed is a tissue replacement composition and an associated tissue replacement method that addresses one or more of the above discussed drawbacks.

SUMMARY OF THE DISCLOSURE

In accordance with one embodiment of the disclosure, a material is provided. The material includes a synthetic organic polymer having a sterile surface with physical structures extending therefrom or defined therein. Each of a substantial number of the physical structures is defined by a set of dimensions where a first dimension of the set is equal to, or less than, about 100 nm and a second dimension of the set is from about 100 nm to about 1 nm.

In accordance with another embodiment of the disclosure, a material is provided. The material includes a synthetic organic polymer having a sterile surface with physical structures extending therefrom or defined therein. Each of a substantial number of the physical structures is defined by a set of dimensions where each dimension of the set is equal to from about 100 nm to about 1 nm.

In accordance with still another embodiment of the disclosure, a material is provided. The material includes a synthetic organic polymer having a sterile surface with physical structures extending therefrom or defined therein. Each of a substantial number of the physical structures is defined by a set of dimensions where each dimension of the set is equal to, or less than, about 100 nm and at least one dimension of the set is from about 1 nm to about 100 nm.

In accordance with yet another embodiment of the disclosure, a method of fabricating a material is provided. The method includes treating a surface of a synthetic organic polymer to cause the creation of physical structures extending from, or defined in, the surface, wherein each of a substantial number of the created physical structures is defined by a set of dimensions where a first dimension of the set is equal to, or less than, about 100 nm and a second dimension of the set is from about 100 nm to about 1 nm. The method also includes sterilizing the surface of the synthetic organic polymer.

In accordance with still another embodiment of the disclosure, a method of fabricating a material is provided. The method includes treating a surface of a synthetic organic polymer to cause the creation of physical structures extending from, or defined in, the surface, wherein each of a substantial number of the physical structures is defined by a set of dimensions where each dimension of the set is equal to from about 100 nm to about 1 nm. The method also includes sterilizing the surface of the synthetic organic polymer.

In accordance with yet another embodiment of the disclosure, a method of fabricating a material is provided. The method includes treating a surface of a synthetic organic polymer to cause the creation of physical structures extending from, or defined in, the surface, wherein each of a substantial number of the physical structures is defined by a set of dimensions where each dimension of the set is equal to, or less than, about 100 nm, and at least one dimension of the set is from about 1 nm to about 100 nm. The method also includes sterilizing the surface of the synthetic organic polymer.

DETAILED DESCRIPTION OF THE DISCLOSURE

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Materials having enhanced animal tissue compatibility are disclosed herein. The materials include a synthetic organic polymer having a sterile surface with physical structures extending therefrom or defined therein. Each of a substantial number of the physical structures is defined by a set of dimensions (including, for example, length, diameter, width, height, parameter, radius, circumference, and depth) where a first dimension of the set is equal to, or less than, about 100 nm and a second dimension of the set is from about 100 nm to about 1 nm.

In another embodiment, it is contemplated that each of a substantial number of the physical structures is defined by a set of dimensions where each dimension of the set is equal to from about 100 nm to about 1 nm. For example, each of the dimensions is equal to from about 90 nm to about 1 nm, or from about 80 nm to about 1 nm, or from about 70 nm to about 1 nm, or from about 60 nm to about 1 nm, or from about 50 nm to about 1 nm, or from about 40 nm to about 1 nm, or from about 30 nm to about 1 nm, or from about 20 nm to about 1 nm, or from about 10 nm to about 1 nm. In another example, each of the dimensions is equal to from about 90 nm to about 10 nm, or from about 90 nm to about 20 nm, or from about 90 nm to about 30 nm, or from about 90 nm to about 40 nm, or from about 90 nm to about 50 nm, or from about 90 nm to about 60 nm, or from about 90 nm to about 70 nm, or from about 90 nm to about 80 nm. Furthermore, it should be appreciated that the above described dimension size ranges only serve an illustrative purpose and are not meant to limit the present disclosure. For example, other dimension size ranges within the aforementioned size range from about 100 nm to about 1 nm are contemplated, such as from about 70 nm to about 20 nm, or from about 85 nm to about 15 nm, and the like.

In another embodiment, it is contemplated that each of a substantial number of the physical structures is defined by a set of dimensions where each dimension of the set is equal to, or less than, about 100 nm and at least one dimension of the set is from about 1 nm to about 100 nm.

Note that it is contemplated that the embodiments of the above described sterile surfaces can define the entire surface of a material described herein, or only a portion of the surface of a material described herein.

It should be understood that, as used herein, "physical structure" includes, but is not limited to, for example, protrusions, ridges, depressions, grooves, and wells disposed on, or in, the sterile surface. It should also be understood that what is meant herein by the phrase "the physical structures is defined by a set of dimensions" is that a set of dimensions such as, combinations of dimensions selected from the group including, for example, length, diameter, width, height, parameter, radius, circumference, and depth define the physical structure. For example, a ridge disposed on a surface of a material described herein will have a length dimension, a width dimension, and a height dimension which defines this physical structure and this set of dimensions satisfies the criteria of one or more of the above described sets of dimensions (e.g., (i) a set of dimensions where a first dimension of the set is equal to, or less than, about 100 nm and a second dimension of the set is from about 100 nm to about 1 nm, (ii) a set of dimensions where each dimension of the set is equal to from about 100 nm to about 1 nm, or (iii) a set of dimensions where each dimension of the set is equal to, or less than, about 100 nm, and at least one dimension of the set is from about 1 nm to about 100 nm).

It should also be understood that what is meant herein by "a substantial number of the physical structures" is that the sterile surface has extending therefrom or defined therein significantly more than a deminimis amount of physical structures defined by one or more of the above described sets of dimensions. What is meant herein by a deminimis amount is an amount of the physical structures defined by one or more of the above described sets of dimensions which would normally be present on a sterile surface as a result of the surface being exposed to its ambient surroundings during, for example, packaging and use thereof. In addition, what is meant herein by "a substantial number of physical structures" includes a sterile surface that has a number or amount of the physical structures defined by the above described set of dimensions effective to increase the tissue compatibility of the sterile surface. For example, as discussed in greater detail below, having a substantial number of physical structures defined by the above described set of dimensions extending from, or defined in, the sterile surface increases animal cell adherence and proliferation on the surface.

It should be appreciated that the material disclosed herein includes synthetic organic polymers. It should be understood that what is meant herein by the phrase "synthetic organic polymers" is an organic polymer that is produced by an artificial rather than a natural process. The synthetic organic polymers included in the material disclosed herein should be cytocompatible. In addition, the synthetic organic polymers can be bioabsorbable and/or bioerodable. The synthetic organic polymers should also be non-toxic, non-carcinogenic, and cause no adverse immunologic response. Representative useful synthetic organic polymers which can be included in the materials disclosed herein include: polyurethane; polyfumarates; polylactides; polyglycolides; polycaprolactones; polyanhydrides; pyrollidones, for example, methylpyrollidone; cellulosic polymers, for example, carboxymethyl cellulose; methacrylates; collagens, for example, gelatin; glycerin and polylactic acid. Synthetic resins, may also be used, including, for example, epoxy resins, polycarbonates, silicones, polyesters, polyethers, polyolefins, synthetic rubbers, polyurethanes, nylons, polyvinylaromatics, acrylics, polyamides, polyimides, phenolics, polyvinylhalides, polyphenyleneoxide, polyketones and copolymers and blends thereof. Copolymers which can be used in the present invention include both random and block copolymers. Polyolefin resins include polybutylene and polyethylene, such as low density polyethylene, medium density polyethylene, high density polyethylene and ethylene copolymers; polyvinylhalide resins include polyvinyl chloride polymers and copolymers and polyvinylidene chloride polymers and copolymers, fluoropolymers; polyvinylaromatic resins include polystyrene polymers and copolymers α-methylstyrene polymers and copolymers; acrylate resins include polymers and copolymers of acrylate and methacrylate esters, polyamide resins include nylon 6, nylon 11, and nylon 12, as well as polyamide copolymers and blends thereof; polyester resins include polyalkylene terephthalates, such as polyethylene terephthalate and polybutylene terephthalate, as well as polyester copolymers; synthetic rubbers include styrene-butadience and acrylunitrile-butadience-styrene coploymers and; polyketones include polyethertones and polyetherketones. Note that the synthetic organic polymer of the present invention are preferably made from polyurethane and/or the biodegradable polymers of polycaprolactone, poly-L-lactic acid, and poly-glycolic acid, as well as the copolymers of poly-L-lactic acid and poly-glycolic acid, since their mechanical properties are similar to collagen present in soft tissue (such as bladder and cardiovascular tissue).

As indicated above, the surface of a material described herein for placing in contact with animal tissue is sterile. The surface of the material may be sterilized using any appropriate conventional sterilization technique as long as it does not significantly weaken the mechanical strength and mechanical properties of the material nor adversely alter the dimensions of the physical structures extending from or defined in the surface. In particular, the sterilization technique does not alter the dimensions of the physical structures in a way that results in a substantial number of the physical structures failing to satisfy the criteria of one or more of the above described sets of dimensions (e.g., the surface of the material no longer has substantial number of physical structures which are defined by (i) a set of dimensions where a first dimension of the set is equal to, or less than, about 100 nm and a second dimension of the set is from about 100 nm to about 1 nm, (ii) a set of dimensions where each dimension of the set is equal to from about 100 nm to about 1 nm, or (iii) a set of dimensions where each dimension of the set is equal to, or less than, about 100 nm, and at least one dimension of the set is from about 1 nm to about 100 nm). For example, the surface of a material described herein can be sterilized by ethanol soaking (in 90% ethanol for 24 hours) and/or UV light exposure for 12 hours.

It should be appreciated that a material described herein can be fabricated, for example, by (i) treating a surface of a synthetic organic polymer to cause the creation of physical structures extending from, or defined in, the surface, where each of a substantial number of the created physical structures is defined by a set of dimensions where a first dimension of the set is equal to, or less than, about 100 nm and a second dimension of the set is from about 100 nm to about 1 nm and (ii) sterilizing the surface of the synthetic organic polymer. It should be appreciated that a material described herein can also be fabricated, for example, by (i) treating a surface of a synthetic organic polymer to cause the creation of physical structures extending from, or defined in, the surface, where each of a substantial number of the physical structures is defined by a set of dimensions and where each dimension of the set is equal to from about 100 nm to about 1 nm and (ii) sterilizing the surface of the synthetic organic polymer. It should further be appreciated that a material described herein can be fabricated, for example, by (i) treating a surface of a synthetic organic polymer to cause the creation of physical structures extending from, or defined in, the surface, where each of a substantial number of the physical structures is defined by a set of dimensions and where each dimension of the set is equal to, or less than, about 100 nm, and at least one dimension of the set is from about 1 nm to about 100 nm and (ii) sterilizing the surface of the synthetic organic polymer.

It should further be appreciated a material described herein can be fabricated, for example, by (i) substantially increasing the number of the above described physical structures extending from or defined in a surface of a synthetic organic polymer or (ii) creating a substantial number of the above described physical structures extending from or defined in a surface of a synthetic organic polymer which only possessed a diminimus number of such physical structures.

Now turning to the fabrication of an exemplary material of the present invention, polymer pellets (0.5 g) are dissolved in 8 ml of an appropriate solvent (for example, chloroform for poly-lactic/glycolic acid, and tetrahydrofuran for polyurethane and polycaprolactone), vortexed, cast, vacuum dried at room temperature for 48 hours, and then cut into three-dimensional scaffolds (1 cm×1 cm×0.5 cm). Synthetic organic polymers with basic functional groups (such as polyurethane) are soaked in acidic solutions (e.g., a $HNO_3$ solution) having a concentration of about, for example 0.1 N to about 10N of for a time period of about, for example, 15 minutes to about 5 hours, while shaking at room temperature. In contrast, synthetic organic polymers with acidic functional groups (such as poly-L-lactic acid, poly-glycolic acid, polycaprolactone and their copolymers) can be soaked in basic solutions, for example NaOH, having a concentration of about, for example, 0.1 N to about 10 N for a time period of about, for example 15 minutes to about 5 hours, while shaking at room temperature.

A sample of a poly-L-lactic acid/poly-glycolic acid copolymer (hereinafter referred to as PLGA) was subjected to the above described procedure. In particular, the 0.5 g of PLGA (purchased from Polysciences, Cat. No. 23986) was dissolved in chloroform, vortexed, cast, vacuum dried at room temperature for 48 hours, and then cut into three-dimensional scaffolds (1 cm×1 cm×0.5 cm). The PLGA scaffolds were then divided into four separate samples, i.e., a control sample, a sample A, a sample B, and a sample C. The control sample was not subjected to any further treatments. However, samples A, B, and C were subjected to the following treatments. The sample A scaffold was soaked in a 0.1 N NaOH solution for ten minutes. After ten minutes the NaOH solution was neutralized with an acid such as HCl. The NaOH solution was then evaporated under reduced pressure to obtain a sheet of synthetic organic polymer material composed of PLGA. The sample B scaffold was soaked in a 5 N NaOH solution for 30 minutes. After the 30-minute time period the NaOH solution was neutralized with an acid such as HCl. The NaOH solution was then evaporated under reduced pressure to obtain a sheet of synthetic organic polymer material composed of PLGA. Sample C was soaked in a 10 N NaOH solution for 60 minutes, after which the NaOH solution was neutralized with an acid such as HCl. The NaOH solution was then evaporated under reduced pressure to obtain a sheet of synthetic organic polymer material composed of PLGA.

Figure 1:
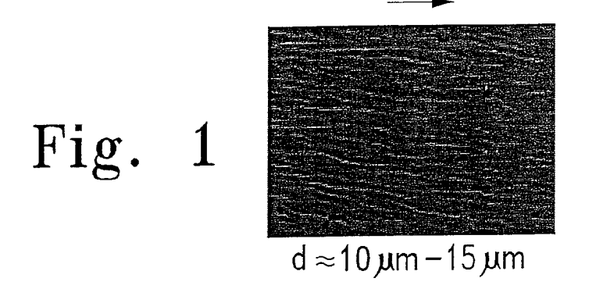
FIG. 1 is a scanning electron micrograph of a sample of poly-L-lactic/poly-glycolic acid copolymer (note that the bar=100 µm)
Figure 2:
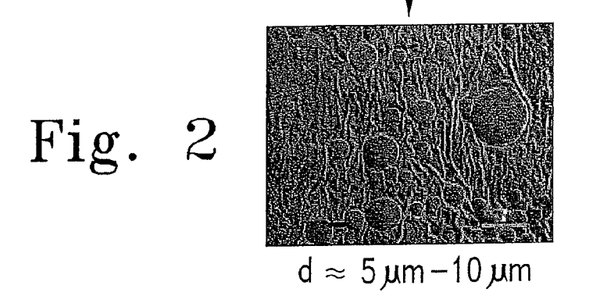
FIG. 2 is a scanning electron micrograph of a sample of poly-L-lactic/poly-glycolic acid copolymer after treating the sample with 0.1 N NaOH for 10 minutes (note that the bar=100 µm)
Figure 3:
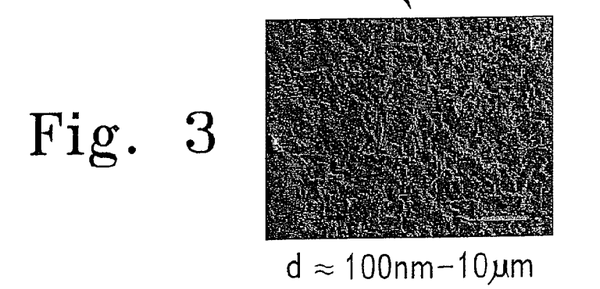
FIG. 3 is a scanning electron micrograph of a sample of poly-L-lactic/poly-glycolic acid copolymer after treating the sample with 5 N NaOH for 30 minutes (note that the bar=100 μm)

As shown in FIG. 1 the control sample of PLGA scaffold, which was not treated with NaOH, has a number of physical structures on the surface thereof having dimensions of about 10 µm to about 15 µm (i.e., d≈10 µm-15 µm; note that the bar in the lower right corner of each scanning electron micrograph equals 100 µm). However as shown in FIG. 2, sample A of the PLGA scaffold, which was treated with 0.1 N NaOH for ten minutes, has a number of physical structures on the surface thereof having dimensions of about 5 µm to about 10 µm (i.e., d≈5 µm-10 µm). Also as shown in FIG. 3, sample B of the PLGA scaffold, which was treated with the 5 N NaOH for thirty minutes, results in sample B having on the surface thereof a number of physical structures having dimensions of about 100 nm to about 10 µm (i.e., d≈100 nm-10 µm). Furthermore, as shown in FIG. 4, sample C of the PLGA scaffold, which was treated with the 10 N NaOH for 60 minutes, has a number of physical structures on the surface thereof having dimensions of about 50 nm to about 100 nm (i.e., d≈50 nm-100 mm).

The surfaces of the above described control and samples were evaluated according to according to standard scanning electron microscope (SEM) techniques (Webster T J, Siegel R W, Bizios R. Osteoblast adhesion on nanophase ceramics. Biomaterials 1999; 20: 1221-1227, incorporated herein by reference) using a JEOL JSM-840 SEM (JEOL USA, Inc., Peabody, Mass.). Briefly, the control and samples were sputter-coated in gold-palladium in the presence of argon gas at room temperature. These coated samples were then visualized at low (250× or 500×), medium (1000×), and high (5000×) magnifications at an accelerating voltage of 5 kV. Dimensions of physical structures on or in the surface of the sample were measured from the SEM images using Adobe Photoshop (Adobe Systems, Inc.) imaging software; physical structure dimensions are reported as ranges and were determined by averaging five different measurements per sample.

Figure 4:
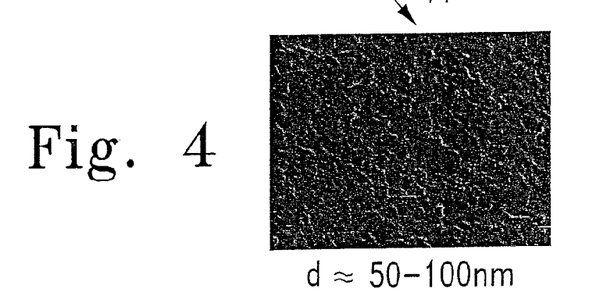
FIG. 4 is a scanning electron micrograph of a sample of poly-L-lactic/poly-glycolic acid copolymer after treating the sample with 10 N NaOH for 60 minutes (note that the bar=100 μm)

Still referring to FIGS. 1-4 it should be understood that treating PLGA in the above described manner results in the physical structures being substantially aligned in a particular direction. In particular as shown in FIG. 2, the physical structures of sample A of the PLGA scaffold, are substantially aligned in the direction indicated by the arrow 10. As shown in FIG. 3, the physical structures of sample B of the PLGA scaffold, are substantially aligned in the direction indicated by the arrow 12. As shown in FIG. 4, the physical structures of sample C of the PLGA scaffold, are substantially aligned in the direction indicated by the arrow 14. It should be understood that the above-described alignment of the physical structures is an advantage of the present invention since such alignment further biomimics the natural proteins that make up natural animal soft tissue, such as bladder, bone, cardiovascular, tendon, and muscle tissues.

It should be appreciated that the ability of a cell to adhere to a material is important to the success of any material to be used to promote tissue growth. In particular, the ability of anchorage-dependant cells (e.g., smooth muscle cells) to adhere to a material is important factor for subsequent cell functioning, such as tissue growth and/or organ regeneration. The below described cell adhesion experiments were conducted as follows. Cells were suspended in recommended media supplemented with serum. The cells were then separately seeded (2,500 cell/cm$^3$) on/in the synthetic organic polymer having a substantial number of physical structures on the surface thereof indicated in FIG. 5 and allowed to adhere to the polymer for 4 hours under standard cell culture conditions. After the prescribed time period, non-adherent cells were removed from each polymer by rinsing with phosphate-buffered saline. Adherent cells were fixed, stained, and counted according to standard techniques. Adherent cell density (cells per unit surface area) were determined by averaging the number of cells in five random fields. Adherent cells were visualized, and the images stored, using Image Pro computer software. All experiments were run in triplicate and were repeated at least three separate times per substrate tested. Data was analyzed using standard analysis of variance "ANOVA" techniques with factorial designs.

Figure 5:
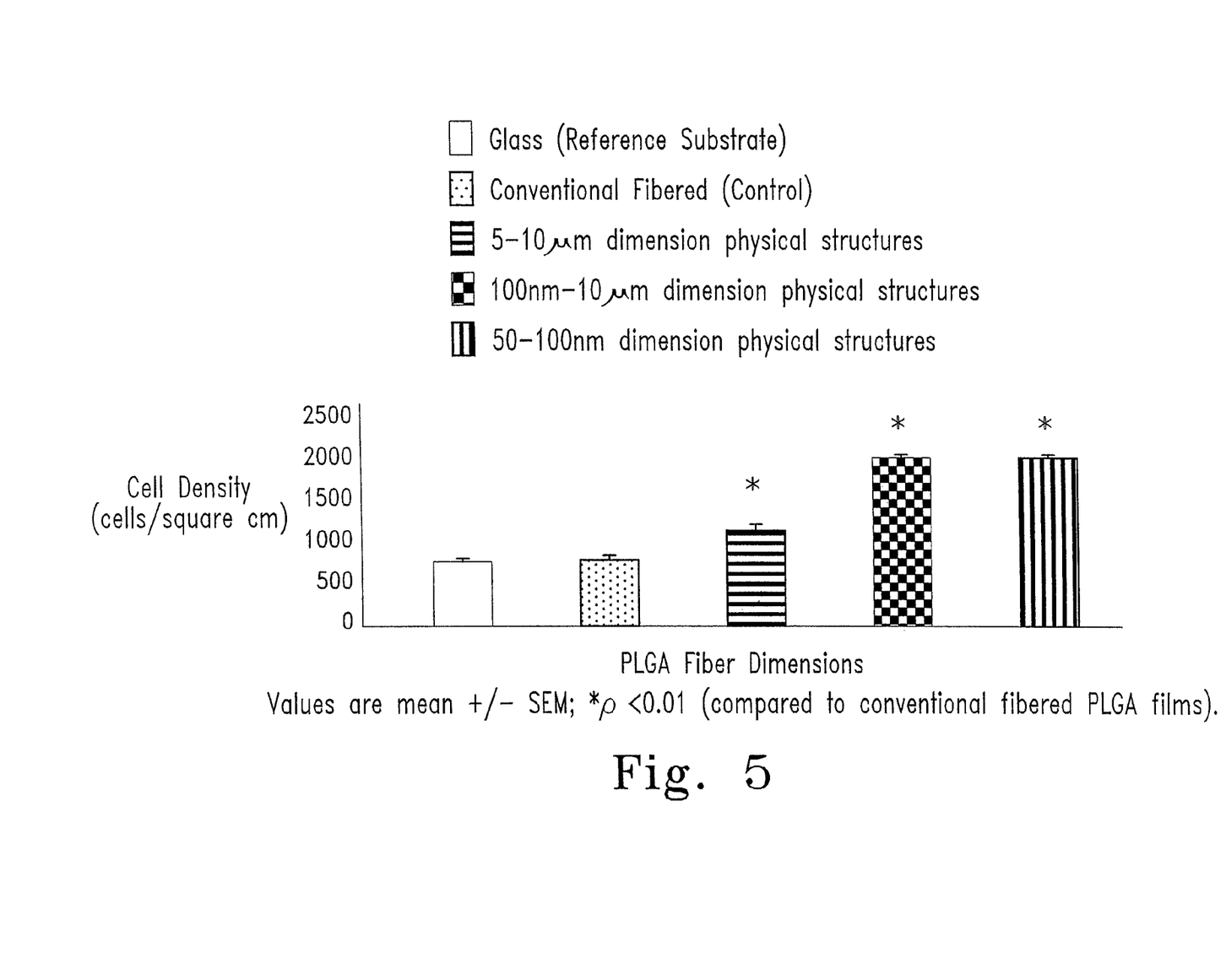
FIG. 5 is a histogram showing adhesion of bladder smooth muscle cells to treated poly-L-lactic/poly-glycolic acid copolymer samples in comparison with adhesion to glass and untreated poly-L-lactic/poly-glycolic acid copolymer sample references.

Now turning to FIG. 5, the data illustrated therein represents the adhesion of bladder smooth muscle cells to the surface of glass (reference substrate), untreated PLGA (control; not treated with NaOH), sample A of PLGA which has, as indicated above, physical structures having dimensions of about 5 µm to about 10 µm, sample B of PLGA which has, as indicated above, physical structures having dimensions of about 100 nm to about 10 µm, and sample C of PLGA scaffold which has, as indicated above, physical structures having dimensions of about 50 nm to about 100 nm. As shown in FIG. 5, bladder smooth muscle cell adhesion was three times greater on sample C as compared to untreated PLGA.

Figure 6:
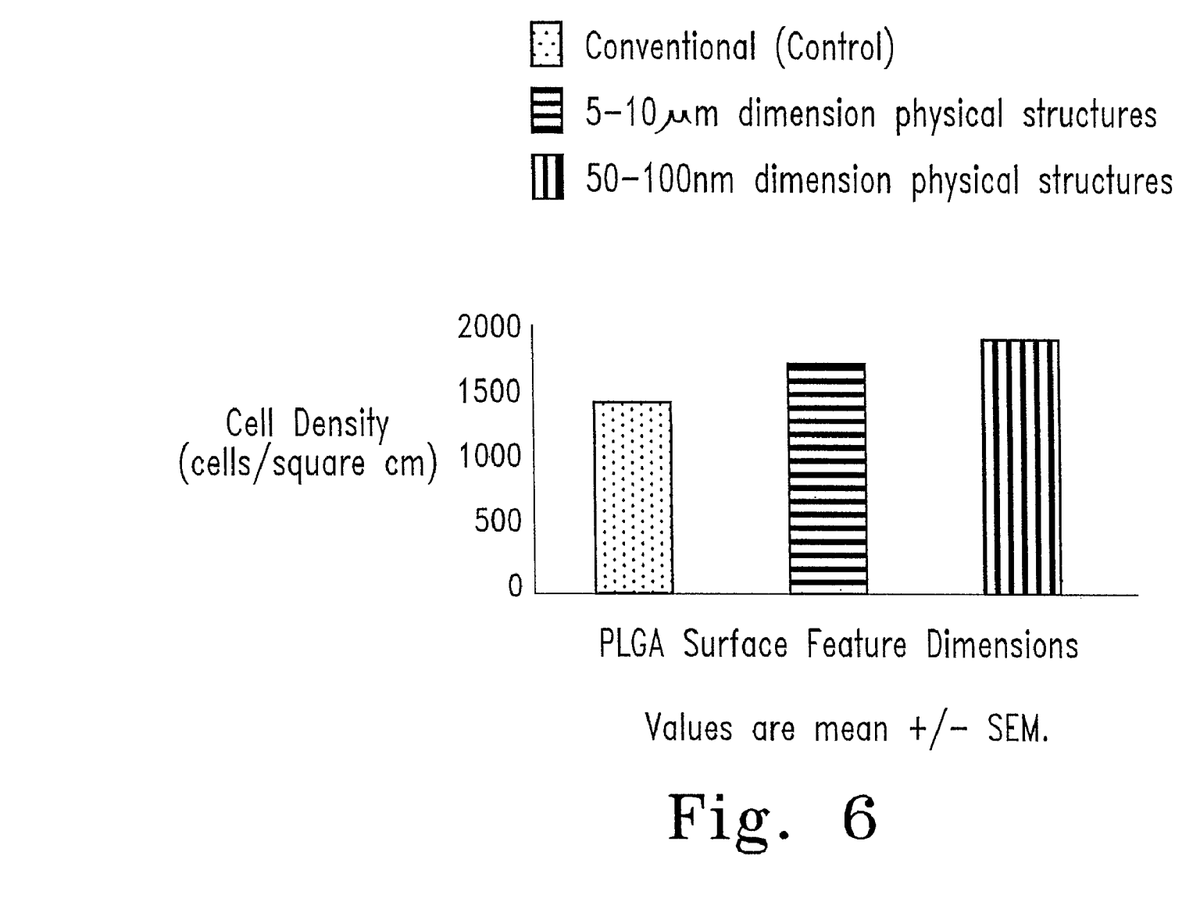
FIG. 6 is a histogram showing adhesion of arterial smooth muscle cells to treated poly-L-lactic/poly-glycolic acid copolymer samples in comparison with adhesion to an untreated poly-L-lactic/poly-glycolic acid copolymer sample reference.

Now turning to FIG. 6, there is shown a similar comparison with the exception that arterial smooth muscle cells were tested for adhesion rather than bladder smooth muscle cells. In particular, the adhesion of arterial smooth muscle cells was tested on untreated PLGA (control; not treated with NaOH), sample A of PLGA which has, as indicated above, physical structures having dimensions of about 5 µm to about 10 µm and sample C of PLGA which has, as indicated above, physical structures having dimensions of about 50 nm to about 100 nm. Similar to the previous data illustrated in FIG. 5, FIG. 6 demonstrates that arterial smooth muscle cells also adhere to samples A and C of the PLGA samples better than untreated PLGA.

Figure 10:
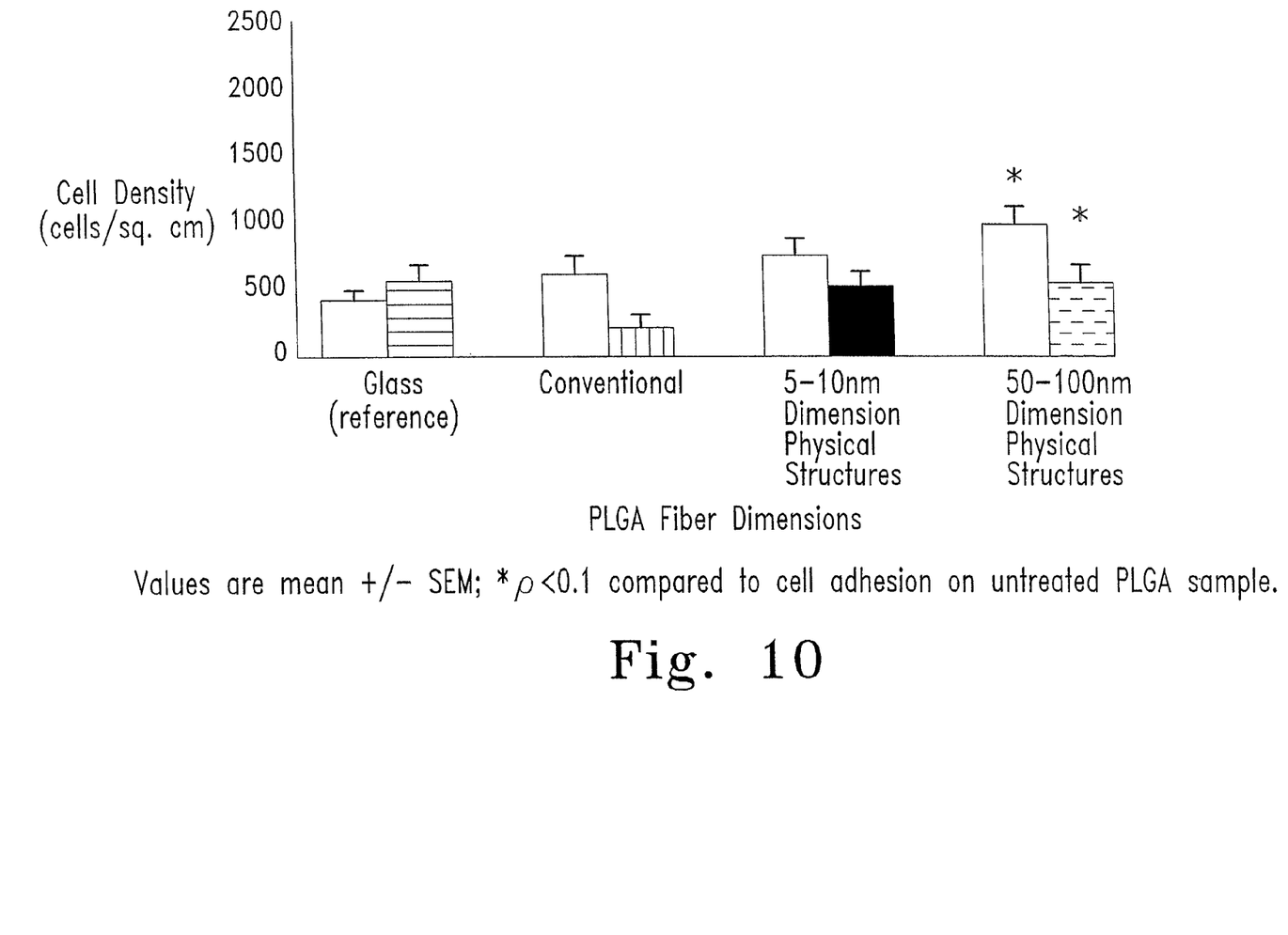
FIG. 10 is a histogram showing adhesion of osteoblasts (□) and chondrocytes (■) to treated poly-L-lactic/poly-glycolic acid copolymer samples in comparison with adhesion to glass and untreated poly-L-lactic/poly-glycolic acid copolymer sample references.

Now referring to FIG. 10, there is shown a similar comparison with the exception that chondrocytes (■) and osteoblasts (☐) were tested for adhesion rather than bladder smooth muscle cells or arterial smooth muscle cells. In particular, the adhesion of chondrocytes and osteoblasts was tested on glass, untreated PLGA (labeled conventional in FIG. 10), sample A of PLGA and sample C of PLGA. Similar to the above discussed data, FIG. 10 demonstrates that chondrocytes and osteoblasts adhere to samples A and C of the PLGA better than untreated PLGA.

It should also be appreciated that the ability of a cell to proliferate (that is, divide) on a material can be important to the success of any material to be used to promote tissue growth. The below described cell proliferation experiments were conducted as follows. Bladder smooth muscle cells were suspended in the recommended media and supplemented with serum. The cells were then separately seeded (2,500 cells/cm$^3$) on/in the substrates indicated in FIG. 7. The cells were then cultured under standard cell culture conditions for 1, 3, and 5 day time periods. At the conclusion of the experiment, the cells were fixed, stained, and counted according to established methods. Cell density (cells per unit surface area) was determined by averaging the number of cells in five random fields.

Figure 7:
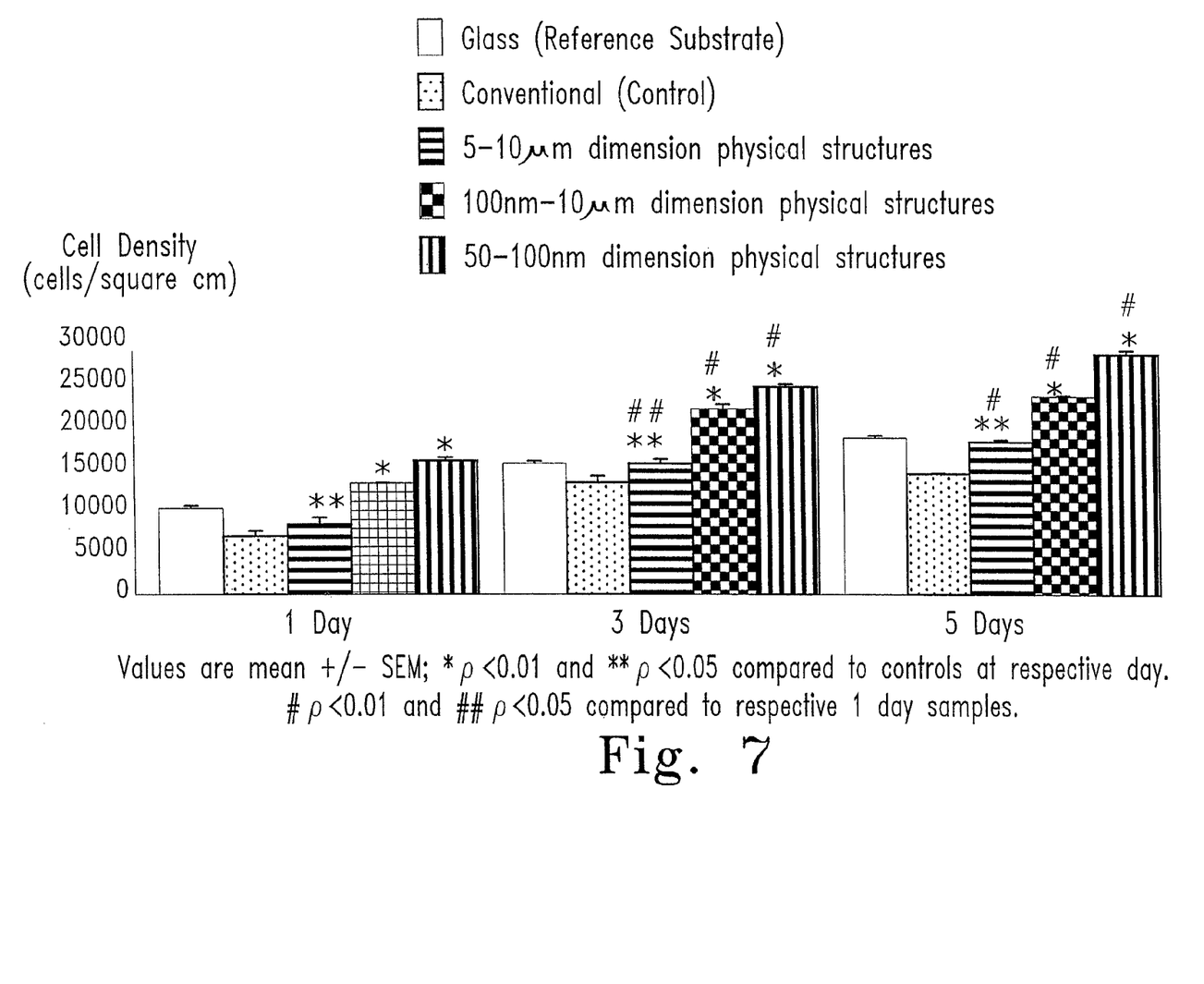
FIG. 7 is a histogram showing bladder smooth muscle cell proliferation on treated poly-L-lactic/poly-glycolic acid copolymer samples in comparison with proliferation on glass and untreated poly-L-lactic/poly-glycolic acid copolymer sample references.

Now turning to FIG. 7, the data illustrated therein represents the proliferation of bladder smooth muscle cells on the surface of glass (reference substrate), untreated PLGA (control; not treated with NaOH), sample A of PLGA (about 5 µm to about 10 µm dimension physical structures), sample B of PLGA (about 100 nm to about 10 µm dimension physical structures) and sample C of PLGA scaffold (about 50 nm to about 100 nm dimension physical structures). FIG. 7 demonstrates that bladder smooth muscle cells proliferate better on samples A, B, and C of the PLGA scaffolds as compared to untreated PLGA.

In another embodiment of the present disclosure, it is contemplated that extra cellular matrix proteins can be utilized to spaciously control specific cell locations on a material of the present invention. For example, disposing an extracellular protein on the inner and outer portions of a sheet of material of the present invention prior to placing the material in contact with animal tissue can selectively control the growth of cells thereon.

Figure 8:
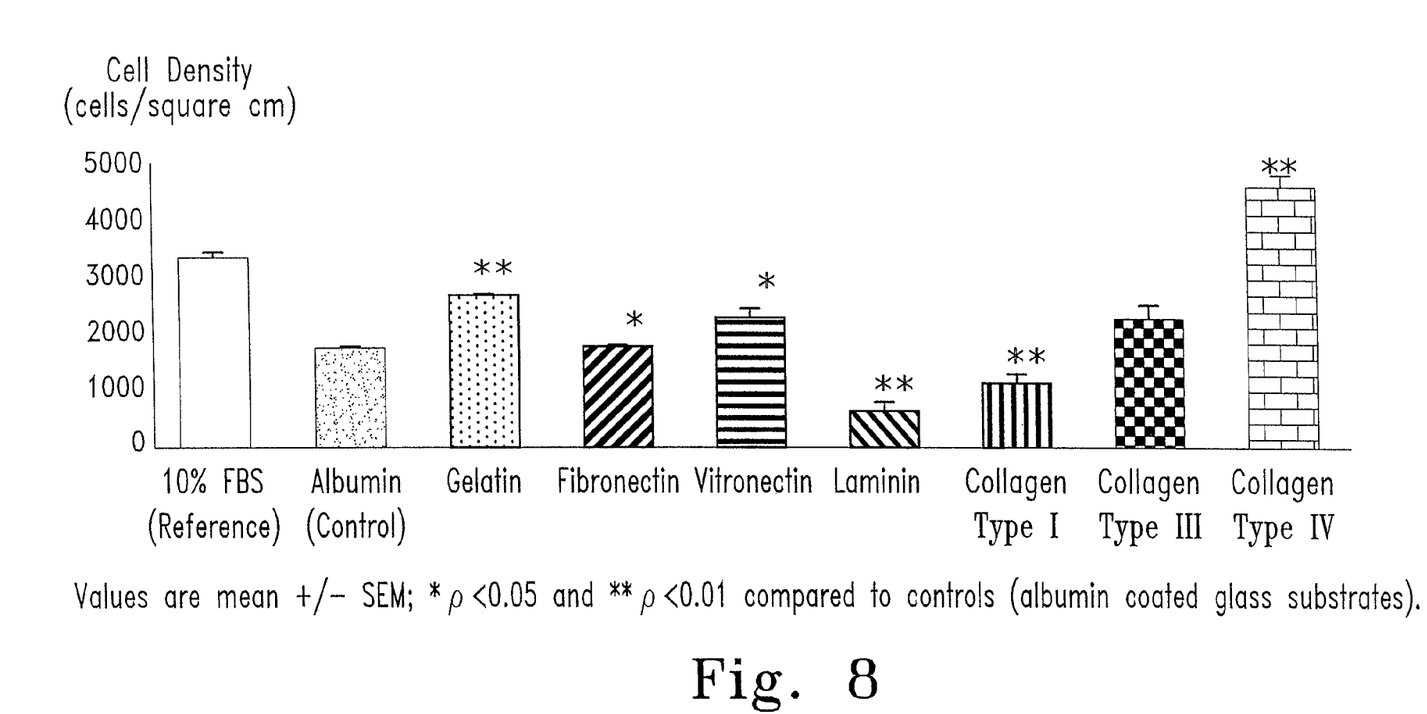
FIG. 8 is a histogram showing adhesion of bladder smooth muscle cells to poly-L-lactic/poly-glycolic acid copolymer samples having different proteins disposed thereon.
Figure 9:
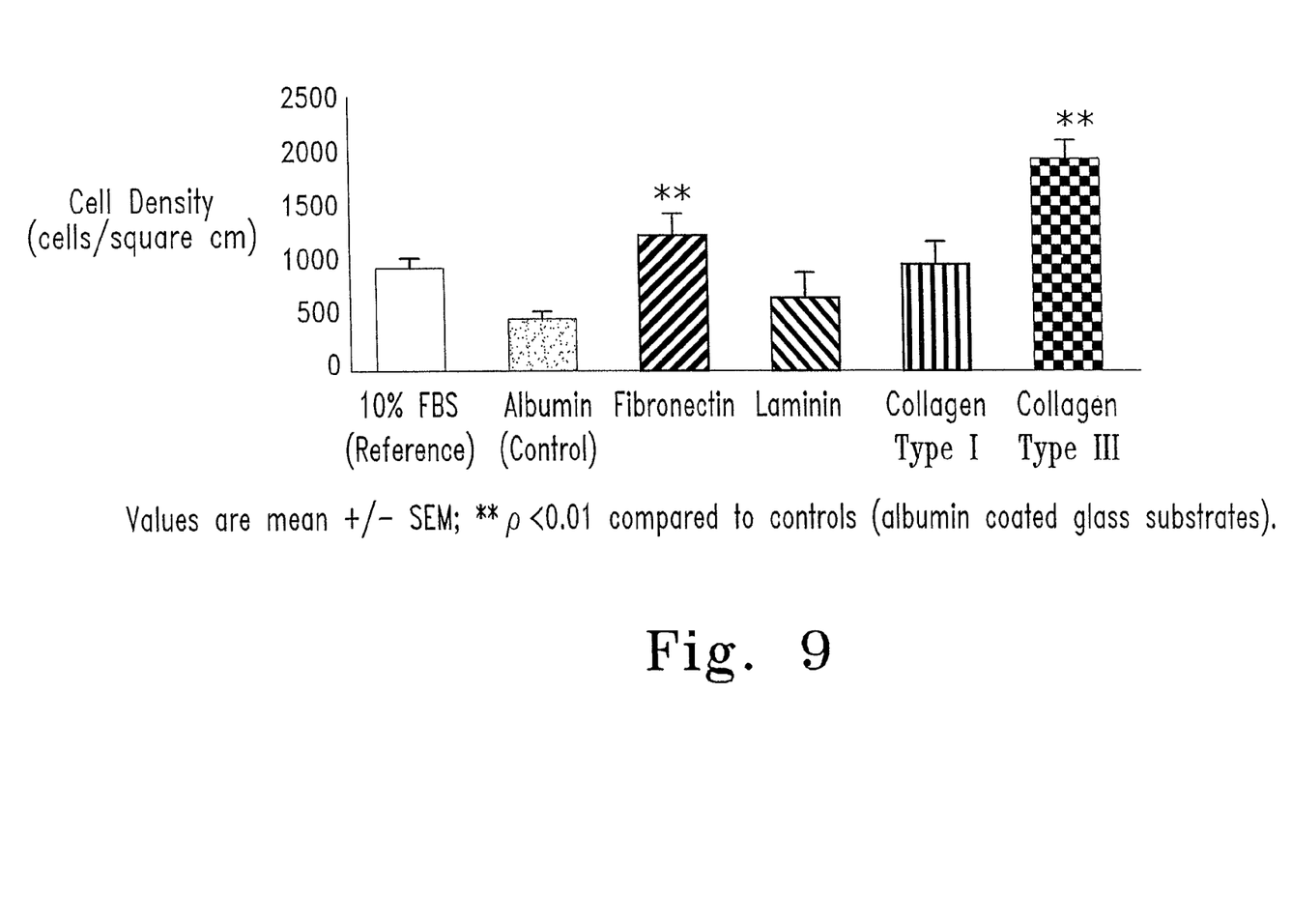
FIG. 9 is a histogram showing adhesion of arterial smooth muscle cells to poly-L-lactic/poly-glycolic acid copolymer samples having different proteins disposed thereon.

In the present disclosure, proteins that control bladder and arterial smooth muscle adhesion were determined by coating borosilicate glass with 5 micrograms/milliter of specific extracellular matrix proteins. Cells were allowed to adhere for four hours at which time they were fixed, stained, and counted. Now turning to FIG. 8, the data represented therein demonstrates that, as compared to other proteins such as albumin, gelatin, fibronectin, vitronectin, laminin, collagen type I, and collagen type III, bladder smooth muscle cell adhesion was significantly greater on the material pretreated with collagen type IV after four hours. Furthermore, as shown in FIG. 9, as compared to other proteins such as FBS, albumin, fibronectin, laminin and collagen type I, arterial smooth muscles cell adhesion was significantly greater on material of the present disclosure pretreated with collagen type III after four hours. In this manner, proteins have been identified to control where a cell will adhere on materials described herein. This is important since cells are found in select regions of natural tissue. For example, the materials described herein could be treated before implantation with identified proteins to control where cells will adhere and proliferate once the polymers are implanted.

Now turning to another synthetic organic polymer which can be utilized in a material described herein: polyurethane. A sample of a polyurethane (hereinafter referred to as PU) was subjected to the above described procedure described for PLGA. In particular, the 0.5 g of PU (purchased from Thermedics, Inc. Cat. No. Tecoflex EG-72D) was dissolved in tetrahydrofuran, vortexed, cast, vacuum dried at room temperature for 48 hours, and then cut into three-dimensional scaffolds (1 cm×1 cm×0.5 cm). The PU scaffolds were then divided into three separate samples, i.e., a control sample, a sample A and a sample B. The control sample was not subjected to any further treatments. However, samples A and B were subjected to the following treatments. The sample A scaffold was soaked in a 0.1 N HNO$_3$ solution for ten minutes. After ten minutes the HNO$_3$ solution was neutralized with a base such as NaOH. The HNO$_3$ solution was then evaporated under reduced pressure to obtain a sheet of polymer material composed of PU. The sample B scaffold was soaked in a 10 N HNO$_3$ solution for 30 minutes. After the 30 minute time period the HNO$_3$ solution was neutralized with a base such as NaOH. The HNO$_3$ solution was then evaporated under reduced pressure to obtain a sheet of synthetic organic polymer material composed of PU.

Figure 11:
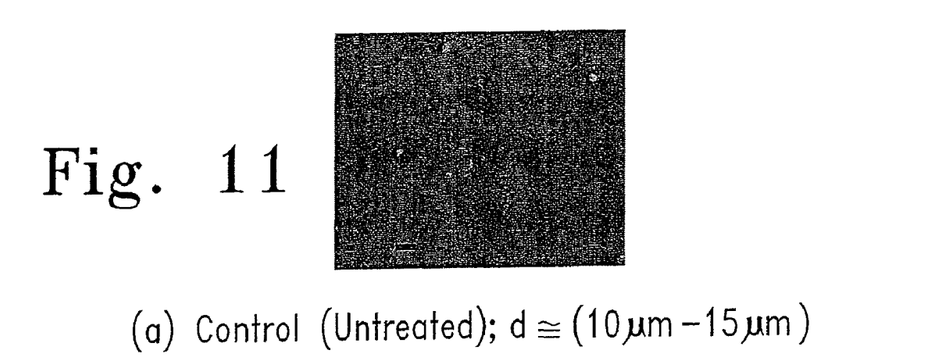
FIG. 11 is a scanning electron micrograph of a sample of polyurethane (note that the bar=1 μm)
Figure 12:
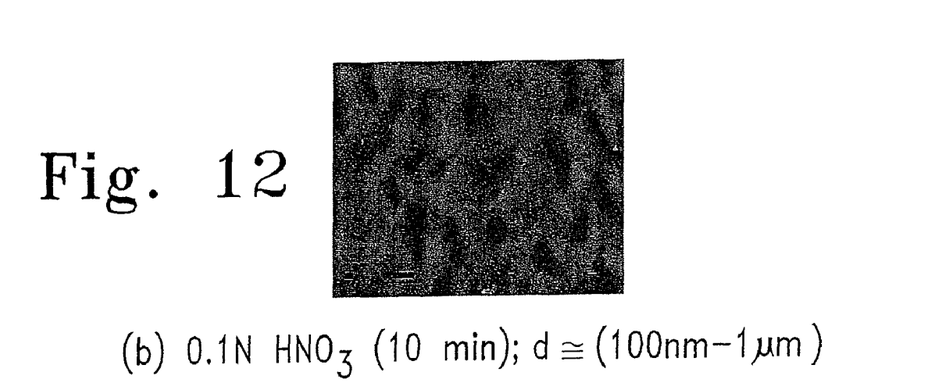
FIG. 12 is a scanning electron micrograph of a sample of polyurethane after treating the sample with 0.1 N HNO3 for 10 minutes (note that the bar=1 μm)
Figure 13:
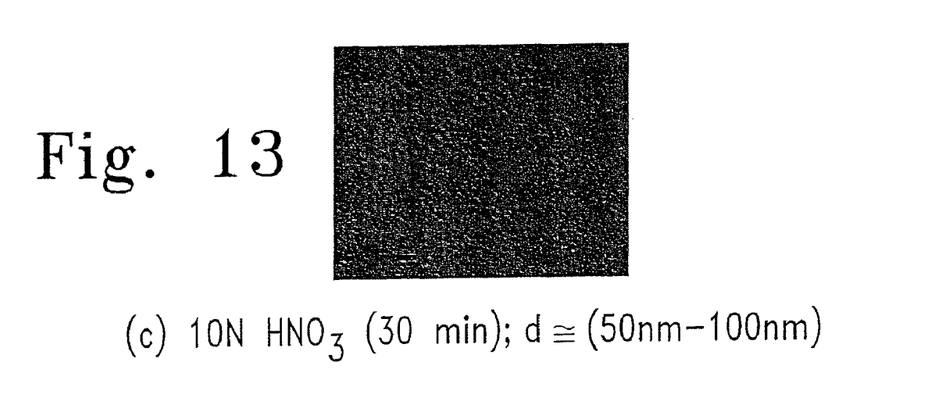
FIG. 13 is a scanning electron micrograph of a sample of polyurethane after treating the sample with 10 N HNO3 for 30 minutes (note that the bar=1 μm)

As shown in FIG. 1 the control sample of PU scaffold, which was not treated with HNO$_3$, has a number of physical structures on the surface thereof having dimensions of about 10 µm to about 15 µm (i.e., d≈10 µm-15 µm; note that the bar in the lower right corner of each scanning electron micrograph equals 1 µm). However as shown in FIG. 12, sample A of the PU scaffold, which was treated with the 0.1 N HNO$_3$ for ten minutes, has a number of physical structures on the surface thereof having dimensions of about 100 nm to about 1 µm (i.e., d≈100 nm-1 µm). Furthermore, as shown in FIG. 13, sample B of the PU scaffold, which was treated with the 10 N HNO$_3$ for 30 minutes, has a number of physical structures on the surface thereof having dimensions of about 50 nm to about 100 nm (i.e., d≈50 nm-100 nm).

Figure 14:
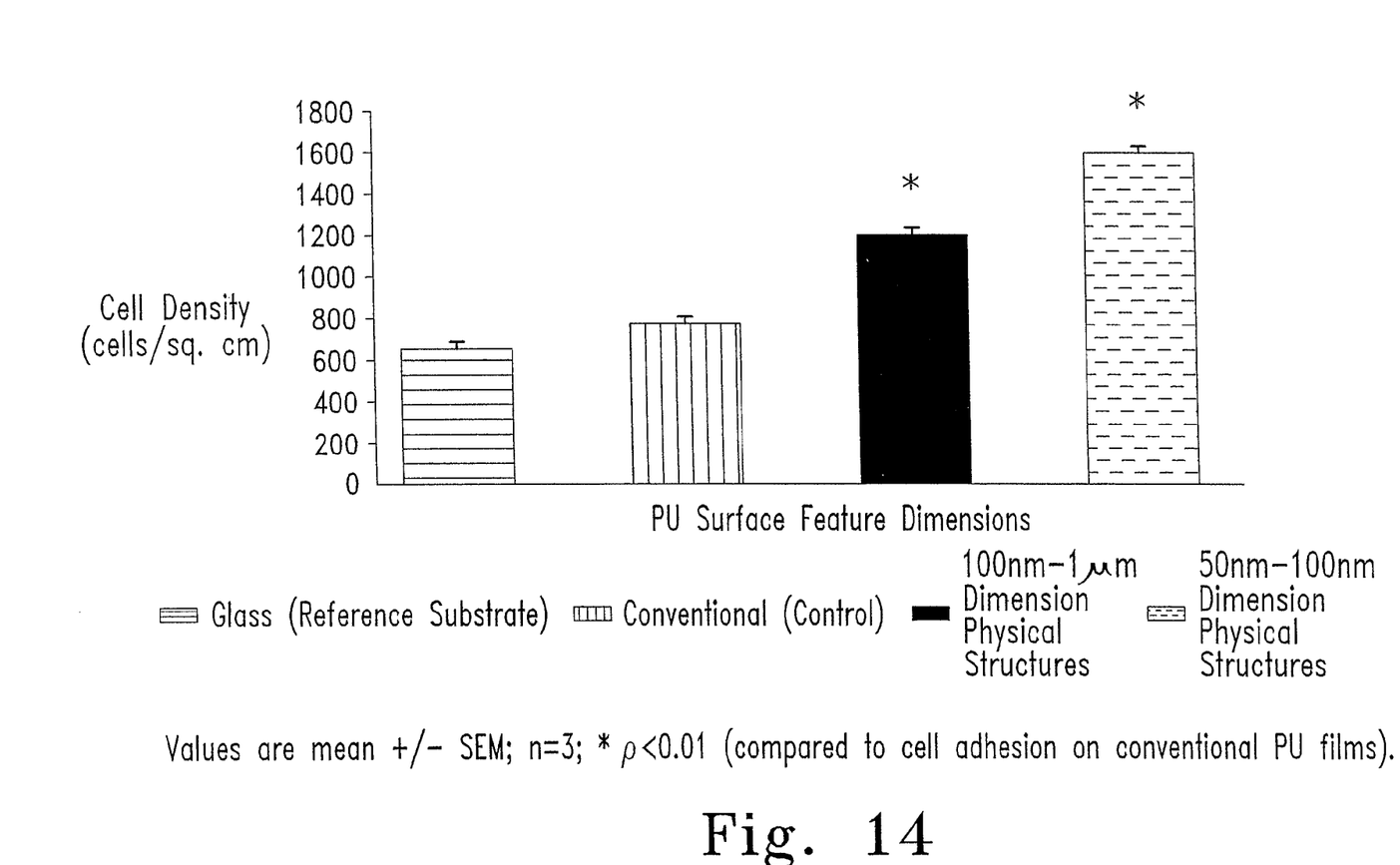
FIG. 14 is a histogram showing adhesion of bladder smooth muscle cells to treated polyurethane samples in comparison with adhesion to glass and untreated polyurethane sample references.

Now turning to FIG. 14, the data illustrated therein represents the adhesion of bladder smooth muscle cells to the surface of glass (reference substrate), untreated PU (conventional; not treated with HNO$_3$), sample A of PU scaffold (physical structure dimensions of about 1 µm to about 100 nm, and sample B of PU scaffold (physical structure dimensions of about 100 nm to about 50 nm). As shown in FIG. 14, as compared to glass or untreated PU, bladder smooth muscle cell adhesion is greater on samples A and B. For example, bladder smooth muscle cell adhesion was two times greater on sample B as compared to untreated PU.

Now turning to another synthetic organic polymer which can be utilized in a material described herein: polycaprolactone. A sample of a polycaprolactone (hereinafter referred to as PC) was subjected to the above described procedure described for PLGA. In particular, the 0.5 g of PC (purchased from Polysciences, Cat. No. 19561-500) was dissolved in tetrahydrofuran, vortexed, cast, vacuum dried at room temperature for 48 hours, and then cut into three-dimensional scaffolds (1 cm×1 cm×0.5 cm). The PC scaffolds were then divided into three separate samples, i.e., a control sample, a sample A and a sample B. The control sample was not subjected to any further treatments. However, samples A and B were subjected to the following treatments. The sample A scaffold was soaked in a 0.1 N NaOH solution for one minute. After one minute the NaOH solution was neutralized with an acid such as HCl. The NaOH solution was then evaporated under reduced pressure to obtain a sheet of polymer material composed of PC. The sample B scaffold was soaked in a 10 N NaOH solution for 10 minutes. After the 10 minute time period the NaOH solution was neutralized with an acid such as HCl. The NaOH solution was then evaporated under reduced pressure to obtain a sheet of polymer material composed of PC.

Figure 15:
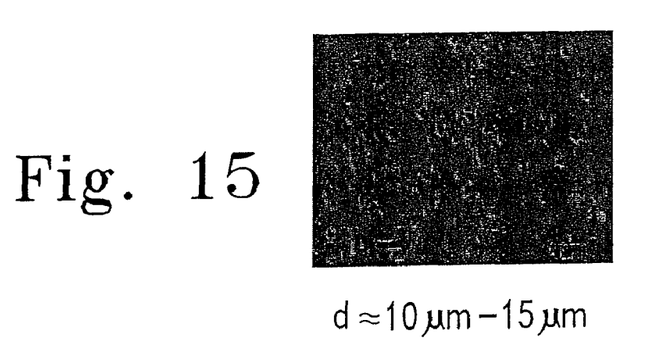
FIG. 15 is a scanning electron micrograph of a sample of polycaprolactone (note that the bar=10 μm)
Figure 16:
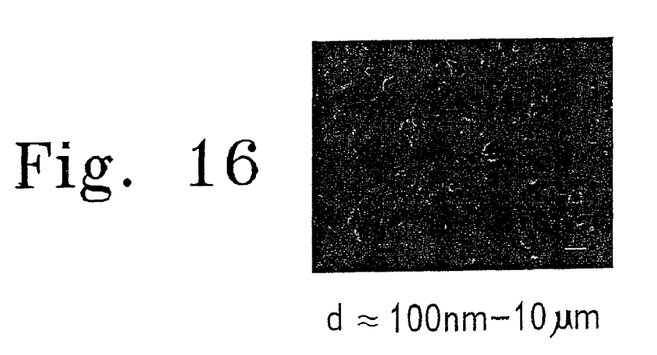
FIG. 16 is a scanning electron micrograph of a sample of polycaprolactone after treating the sample with 0.1 N NaOH for 1 minute (note that the bar=10 μm)
Figure 17:
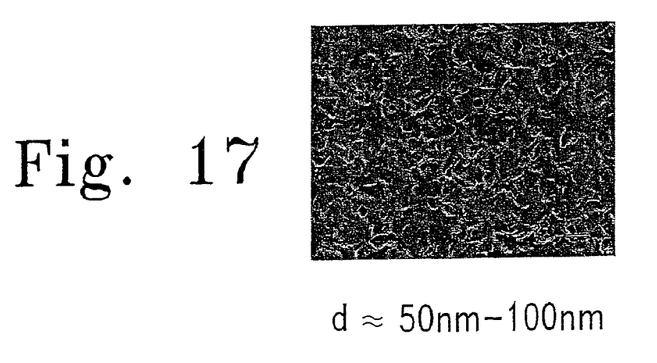
FIG. 17 is a scanning electron micrograph of a sample of polycaprolactone after treating the sample with 10 N NaOH for 10 minutes (note that the bar=10 μm).

As shown in FIG. 15 the control sample of PC scaffold, which was not treated with NaOH, has physical structures on the surface thereof having dimensions of about 10 μm to about 15 μm (i.e., d≈10 μm-15 μm; note that the bar in the lower right corner of each scanning electron micrograph equals 10 μm). However as shown in FIG. 16, sample A of the PC scaffold, which was treated with the 0.1 N NaOH for one minute, has physical structures on the surface thereof having dimensions of about 100 nm to about 10 μm (i.e., d≈100 nm-10 nm). Furthermore, as shown in FIG. 17, sample B of the PU scaffold, which was treated with the 10 N NaOH for 10 minutes, has physical structures on the surface thereof having dimensions of about 50 nm to about 100 nm (i.e., d≈50 nm-100 nm).

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected.

The invention claimed is:

1. A composition, comprising:
    a synthetic organic polymer construct, wherein a surface of said polymer construct comprises a substantial number of physical structures extending therefrom or defined therein, wherein said physical structures comprise protrusions and depressions, and wherein the protrusions have a maximum cross-sectional diameter and maximum height independently selected from a range of about 1 to less than 100 nm, and the depressions have a maximum cross-sectional diameter and maximum depth independently selected from a range of about 1 to less than 100 nm.

2. The composition of claim 1 wherein the synthetic organic polymer is selected from the group consisting of polyurethane, polycaprolactone, poly-L-lactic acid, polyglycolic acid and co-polymers thereof.

3. The composition of claim 1 wherein the material is shaped into a desired three-dimensional structure.

4. The composition of claim 3 wherein only a portion of said surface comprises a substantial number of said physical structures.

5. The composition of claim 4 wherein the synthetic organic polymer is selected from the group consisting of polyurethane, polycaprolactone, poly-L-lactic acid, polyglycolic acid and co-polymers thereof.

6. The composition of claim 1 wherein each of said maximum cross-sectional diameters, maximum height and maximum depth have dimensions selected from a range of about 20 to about 70 nm.

7. A composition, comprising:
    a synthetic organic polymer construct, wherein a surface of said polymer construct comprises a substantial number of physical structures extending therefrom or defined therein, wherein said physical structures comprise ridges and grooves, wherein the ridges have a maximum width and maximum height independently selected from a range of about 20 to about 70 nm, and the grooves have a maximum width and maximum depth independently selected from a range of about 20 to about 70 nm.

8. The composition of claim 7 wherein said ridges and grooves are substantially aligned in one direction.

9. The composition of claim 8 wherein only a portion of said surface comprises said physical structures.

10. The composition of claim 7 wherein the synthetic organic polymer is selected from the group consisting of polyurethane, polycaprolactone, poly-L-lactic acid, polyglycolic acid and co-polymers thereof.

11. The composition of claim 7 wherein the material is shaped into a desired three-dimensional structure.

12. The composition of claim 11 wherein only a portion of an external surface of the three dimensional structure comprises a substantial number of said physical structures.

13. The composition of claim 12 wherein the synthetic organic polymer is selected from the group consisting of polyurethane, polycaprolactone, poly-L-lactic acid, polyglycolic acid and co-polymers thereof.

14. A composition comprising:
    a synthetic organic polymer construct, wherein a surface of said polymer construct comprises a substantial number of physical structures extending therefrom or defined therein, wherein said physical structures comprise protrusions and depressions, and wherein the protrusions have a maximum cross-sectional diameter and maximum height independently selected from a range of about 1 to about 50 nm, and the depressions have a maximum cross-sectional diameter and maximum depth independently selected from a range of about 1 to about 50 nm.

15. The composition of claim 1 wherein one of said maximum cross-sectional diameters, maximum height and maximum depth is selected from a range of about 40 nm to about 90 nm.

* * * * *